US008809308B2

(12) United States Patent
Palepu et al.

(10) Patent No.: US 8,809,308 B2
(45) Date of Patent: Aug. 19, 2014

(54) ENEMA COMPOSITION FOR TREATMENT OF ULCERATIVE COLITIS HAVING LONG TERM STABILITY

(71) Applicant: SciDose, LLC, Amherst, MA (US)

(72) Inventors: Nagesh R. Palepu, Southampton, PA (US); Philip Christopher Buxton, Great Dunmow (GB)

(73) Assignee: SciDose, LLC, Amherst, MA (US)

( * ) Notice: Subject to any disclaimer, the term of this patent is extended or adjusted under 35 U.S.C. 154(b) by 0 days.

(21) Appl. No.: 14/076,560

(22) Filed: Nov. 11, 2013

(65) Prior Publication Data

US 2014/0135299 A1  May 15, 2014

Related U.S. Application Data

(60) Provisional application No. 61/724,678, filed on Nov. 9, 2012.

(51) Int. Cl.
*A61K 31/56* (2006.01)
*A61K 31/58* (2006.01)
*A61K 31/196* (2006.01)
*A61K 31/353* (2006.01)

(52) U.S. Cl.
CPC .............. *A61K 31/58* (2013.01); *A61K 31/196* (2013.01); *A61K 31/353* (2013.01)
USPC .......................................... 514/169; 514/177

(58) Field of Classification Search
CPC ..... A61K 31/56; A61K 31/573; A61K 47/22; A61K 9/08
See application file for complete search history.

(56) References Cited

U.S. PATENT DOCUMENTS

| 4,211,777 | A | 7/1980 | Chambers |
| 4,657,900 | A | 4/1987 | Powell |
| 4,980,173 | A | 12/1990 | Halskov |
| 5,082,651 | A | 1/1992 | Healey |
| 5,084,481 | A | 1/1992 | Ulrich et al. |
| 5,378,470 | A | 1/1995 | Lahr |
| 5,563,131 | A | 10/1996 | Berliner et al. |
| 5,569,670 | A | 10/1996 | Weischer et al. |
| 5,728,735 | A | 3/1998 | Ulrich et al. |
| 5,817,630 | A | 10/1998 | Hofmann et al. |
| 5,945,127 | A | 8/1999 | Breitenbach et al. |
| 6,197,749 | B1 | 3/2001 | Hamuro et al. |
| 6,262,019 | B1 | 7/2001 | Keller et al. |
| 6,444,221 | B1 | 9/2002 | Shapiro et al. |
| 6,605,637 | B1 | 8/2003 | Harnett |
| 6,664,287 | B2 | 12/2003 | Avery et al. |
| 6,887,894 | B2 | 5/2005 | Krämer et al. |
| 7,157,444 | B2 | 1/2007 | Nelson |
| 7,312,243 | B1 | 12/2007 | Pravda |
| 8,476,233 | B2 * | 7/2013 | Pravda ......................... 514/13.2 |
| 2003/0235571 | A1 | 12/2003 | Gojon-Romanillos |
| 2005/0090553 | A1 | 4/2005 | Shapiro |
| 2005/0260140 | A1 | 11/2005 | White et al. |
| 2006/0160904 | A1 | 7/2006 | Caffrey et al. |
| 2006/0193877 | A1 | 8/2006 | Tengler |
| 2006/0264408 | A1 | 11/2006 | Haj-Yehia |
| 2007/0225217 | A1 | 9/2007 | Chappell |
| 2007/0269379 | A1 | 11/2007 | Mitragotri |
| 2008/0066741 | A1 | 3/2008 | LeMahieu |
| 2008/0107650 | A1 | 5/2008 | Tartaglia |
| 2008/0234380 | A1 | 9/2008 | Shapiro |
| 2009/0181081 | A1 | 7/2009 | Gojon-Romanillos |
| 2009/0220583 | A1 | 9/2009 | Pereswetoff-Morath |
| 2011/0142855 | A1 | 6/2011 | Armer |
| 2012/0322773 | A1 | 12/2012 | Pravda |
| 2013/0344184 | A1 | 12/2013 | Pravda |

FOREIGN PATENT DOCUMENTS

| CA | 2097732 | 12/2002 |
| WO | WO00/59899 | 10/2000 |
| WO | WO02/089796 | 11/2002 |
| WO | WO2004/071488 A1 | 6/2004 |
| WO | WO2010/118365 | 10/2008 |

OTHER PUBLICATIONS

Christl, S.U. et al. "Antagonistic effects of sulfide and butyrate on proliferation of colonic mucosa: a potentail role for these agents in the pathoganesis of ulcarative colitis", *Digestive diseases and solences*, 1997, 41(12): 2477-81, abstract only.
Kolgazi, Meltem et al. "α-Lipoic acid modulates gut inflammation induced by tribitrobenzene sulfonic acid in rats", *Journal of Gastroentaclogy and Hispatology*, 2007, 22: 1859-1865.
Pravda, Jay "Radical Induction therapy of ulcerative colits", *World Journal of Gastroenterology*, 2005, 11(18):2371-2384.
Santhanam, Srikanth et al. "Impairment of Milochandrial acetoacetyl CoA thiolase activity in the colonic mucose of patients with ulcerative colitis", *Free Radical Research Communications*, 1993, 18(2):115-122. abstract only.
Sehirli, O et al. "Antioxidant effect of alpha-lipolc acid against ethanol-induced gastrix mucosalemusion in rats", *Pharmacology*, 2008, 81(2): 173-180.
Suzuki YJ et al. "Antioxicant activities of dehydrolipic acid and its structural homologues", *Free Radical Research Comm.*, 1983, 18(2): 115-122, abstract only.
Abraham, N. et al. "Is smoking an indirect risk factor for the development of ulcerative colitis? An age and sex-matched case-control study." *Journal of Gastroenterology and Hepetology*, 2003, pp. 139-146, vol. 18, No. 2.
Allison, M. C. et al. "Prevalence of prodmal fecal stanis in active ulcerative colitis". *Gut*, 1981, pp. 179-182, vol. 32, No. 2.

(Continued)

*Primary Examiner* — Kevin E Weddington
(74) *Attorney, Agent, or Firm* — Lucas & Mercanti, LLP

(57) ABSTRACT

Long term storage stable budesonide-containing solutions are disclosed. The solutions can include budesonide or a pharmaceutically acceptable salt thereof, cromolyn sodium, antioxidizing agent, benzoic acid, and a pharmaceutically acceptable fluid including propylene glycol and water. Kits including the long term storage stable budesonide-containing solutions and methods of treating ulcerative colitis are also disclosed.

29 Claims, No Drawings

(56) References Cited

OTHER PUBLICATIONS

Aw, T. Y. "Molecular and cellular responses to oxidative stress and changes in oxidallon-reduction Imbalance in the intestine" *Am. J. Clin Mats.*, 1999, pp. 557-585, vol. 70.

Bagchi, D. et al. "Stress, Diet and Alcohol-induced Oxidative Gastroinlesfinal Mucosal Injury in Rats and Protection by Bismuth Subsalicylate". *J. Appl. Toxicol*, 1998, pp. 3-13, vol. 18, No. 1.

Bailey, S. M. et al. "Ethanol Stimulates the Production of Reactive Oxygen Species al Milochandrial Complexes I and III". *Free Radical Biology and Medicine*, 1999, pp. 891-900, vol. 27, Nos. 7-8.

Basit, A. et al. "Perspectives on Colonic Drug Delivery" *Pharmatech*, 2003, pp. 185-190, ed. Business Briefings Ltd, London, England.

Batist, G. et al "Interindividual variation in phase II detoxification enzymes in normal human colon mucose" *Biochemical Pharmacology*, 1988, pp. 4241-4243, vol. 37, No. 21.

Beaugerie, L. et al. "Impact of Cessation of Smoking on the Course of Ulcerative Colitis" *The American Journal of Gastroerology*, 2001, pp. 2113-2116, vol. 96, No. 7.

Benson, K.W. et al. "Fecal Inspection"*Am. J.M. Sc.* 1938, pp. 541-545, vol. 198.

Bertz, R. J. et al. "Use of In-Vitro and In-Vivo Date to Estimate the Liklihood of Metabolic Pharmacokinetic Interactions" *Clinical Pharmacokinetics*, Mar. 1997, pp. 210-258, vol. 32, No. 3.

Bilotta, J.J. et al. "Hydrogen peroxide entantis the snow white slgn" Gastrointestrial *Endoscopy*, Sep.-Oct. 1989, pp. 426-430, vol. 35, No. 5.

Black, O.A. et al. "Transit Time in Ulcerative Colitis" *Scand. J. Gastroanlanol*, 1987, pp. 872-875, vol. 22.

Blau, S. et al. "Differences in the reducing power along the rat GI tract: Lower antioxdident capacity of the colon" *Molecular and Cellular Biochemistry*, 1999, pp. 185-191, vol. 194.

Blaut, M. "Assessment of bacteria in the gut microbial ecosystem" *In Intestinal Bone, European Concentrated Action*, Chapter 2, 2000, pp. 1-3.

Boveris, A. et al. "The Cellular Production of Hydrogen Peroxide" *Biochem, J.* 1972, pp. 617-630, vol. 128.

Boveris, A. et al. "The Milochandrial General of Hydrogen Peroxide" *Biochem, J.* 1973, pp. 707-716, vol. 134.

Boveris, A. et al. "Mitochondrial Production of Hydrogen Peroxide Regulation by Nitric Oxide and the Role of Ubisemiquinone" *Life*, 2000, pp. 245-250, vol. 80.

Brunner, L.S. et al. "Perloperefive Management of the Surgical Patient" in *Textbook of Medical Surgical Nursing* 4th edition, 1980, p. 358, Lippincott, Philadelphia.

Buetler, E. et al. "Ethnic Variation in Red Cell Giuiathione Peroxidase activity" *Blood*, Jul. 1975, pp. 103-110, vol. 46, No. 1.

Cadenas, E., et al. "Mitochondrial Free Radical Genenidon, Oxidative Stress, and Aging" *Free Radical Biology & Medicine*, 2000, pp. 222-230, vol. 29, Nos. 3-4.

Caprari, P. et al. "6-Phosphogluconate dehydrogenase deficiency in an Italian family" *Ann. Hamatch*, 2001, pp. 41-44, vol. 80.

Carpenter, H.A. et al. "The Imporatance of Clinecopathological Correlation in the Diagnosis of Imflammatory Conditions of the Colon: Histological Pattern With Critical Implications" *The American Journal of Gastroenterology*, 2000, pp. 878-896, vol. 96, No. 4

Chance, B. et al. "Hydroperoxide Metabolism in Mammalian Organs" *Physiological Reviews*, Jul. 1979, pp. 527-605, vol. 59, No. 3.

Chen, N. et al. "Physiologic concentrations of homocyaine inhibit the human plasms GSH peroxidase that reduces organic hydroperoxides"*J. Lab. Clin. Med*, 2000, pp. 58-85, vol. 136, No. 1.

Chen, S. et al. "Hydroxyl-radical producton in physiological reactions—A novel function of peroxidase" *Eur. J. Biochem*, 1999, pp. 725-735, vol. 280, No. 8.

Ciftci, M. et al. "Effects of Some Drugs on Rat Erythrocyte 6-Phosphogloconal Dehydragensus: An In Vitro and In Vivo Study" *Polish Journal of Pharmagology*, 2002, pp. 276-280, vol. 54.

Cho, J. H. et al. "Identification of novel susceptibility locl for inflammatory bowel disease on chromosomes 1p, 3q, 4q: Evidence for apistacle between 1p and 18D1" *Proc. Natl. Acad. Sci USA*, Jun. 1996, pp. 7502-7507, vol. 95.

Cho, J. H. et al. "Linkage and linkage disequilbrium in chromosome band 1p36 in American Chaldeans with infractory bowel disease" *Human Molecular Genetics*, 2000, pp. 1425-1432, vol. 9, No. 9.

Dalekos G. N. et al. "Zinc, copper and immunological markers in the circulation of well nourished patients with tricerative coltis" *Eur. J. Gastroentarol Hapatol*, Apr. 1998, pp. 331-337, vol. 10, No. 4, abstract only.

Davidson, R. G. "Electrophoretic varients of human-6-phosphogluconate dehydrogenese; population and family studies and description of a new variant" *Ann. Hum. Geriol*, 1957, pp. 355-361, vol. 30.

Davies, K.J.A. "Oxidative Stress, Antioxidard Defenses, and Denage Removal, Repair and Replacement Systems" *Life*, 2000, pp. 279-289, vol. 50.

Dern, R. J. et al. "Hereditary variation of acythrocylic 6-phosphogluconate dehydrogenase" *J. Leb. & Clin. Med.*, Feb. 1966, pp. 255-264, vol. 87, No. 2.

Drossman, D. et al. "Rome II: the function gastrointestinal disorders: diagnosis pathophysiology, and treatment: a multination consensus" *The Functional Gastrointestinal Disorders*, eds. Douglas A. Dross, Enrico Corazziori, 2000, Library of Congress Cataloging-in-Publication Data.

Drossman, D. A. et al. "U.S. Householder Survey of Functional Gastrointestinal Disorders. Pravalence, Sociodemography; and Health Impact" *Digestive Diseases and Sciences*, Sep. 1993, pp. 1539-1580, vol. 38, No. 9.

Duncan, G.G. "Folic Acid (Folacin)" In *Diseases of Metabolism—Detailed Methods of Diagnosis and Treatment* 5th action, 1964, W.S. Saunders Company, Philadelphia and London.

Eaton, J.W. et al. "Acatasiaserente" in *The Metabolic & Molecular Bases of Inherited Disease,* 7th edition, Chapter 74, eds., Scriver C. R. et al., 1996, pp. 2371-2379, McGraw-Hill Medical Publishing Division.

Eaton, J.W. et al. "Molecular Bases of Cellular Iron Toxicity" *Free Radical Biology & Medicine*, 2002, pp. 833-840, vol. 32, No. 2.

Eberhardt, M. K. in *Reactive Oxygen Metebollas—Chemistry and Medical Consquences*, 2001, pp. 23, 51, 63, 64, 81, 118, 125, and 262, CRC Press.

Elsborg, L. et al. "Folate Deficiency in Chronic Inflammatory Bowel Diseases" *Scind J. Gestroant*, 1979, pp. 1019-1024, vol. 14, No. 8.

Everhart, J.E. et al. "A Longitudinal Survey of Self-Reported Bowel Habits in the United States" *Digestive Diseases and Sciences*, Aug. 1989, pp. 1153-1182, vol. 34, No. 8.

Everson, C.A. et al. "Systemic bacterial invasion induced by sleep deprivation" *Am. J. Physiol. reguistory Integrative Comp Physiol.*, 2000, pp. R905-R916, vol. 278.

Farrell, R. J. et al. "Ulcerative colitis" *The Lancet*, Jan. 25, 2002, pp. 331-340, vol. 359.

Farrokhar, F. et al. "A Critical Review of Epidemiological Studies in Inflammatory Bowel Disease " *Scand. J. Gasiroenthavol*, 2001, pp. 2-15, vol. 36, No. 1.

Fernandez-Sanares, F. et al. "Vitamin Status in Patients with Inflammatory Bowel Diseases" *The American Journal of Gastroenterology*, 1969, pp. 744-748, vol. 84, No. 7.

Fowler, J. S. et al. "Monoamine Oxidase and Cigarette Smoking" *Neuro-Toxicology*, 2003, pp. 75-82, vol. 24, No. 1.

Fridovich, I, "Oxygen Toxicity: A Radical Explanation" *The Journal of Experimental Biology*, 1996, pp. 1203-1209, vol. 201.

Friedman G. et al. "A Common Metalion A1298C in Human Methylametatrahydmlolate Reduction Gene: Association with Plasma Gene: Association with Plasma Total Homocyataine and Folate Concentrations" *J. Nutr.*, 1999, pp. 1656-1661, vol. 129, No. 9.

Geerling, B. J. et al. "Diet as a Risk Factor for the Development of Ulcerative Colitis." *The American Journal of Gastroenterology*, Apr. 2000, pp. 1008-1013, vol. 95, No. 4.

Gogua, F. et al., "Thyroid Hormones and Mitcohondria"*Bioscience Reports*, Feb. 2002, pp. 17-29, vol. 22, No. 1.

(56) References Cited

OTHER PUBLICATIONS

Gordillo, E. et al. "Implication of Lysina Residues in the Loss of 6-Phosphoglucorate Dehydrogerase Activity in Aging Human Erythrocytes" *Mechanisms of Ageing and Development*, 1991, pp. 291-297, vol. 59, No. 3.

Goyette, P. et al. "Gene structure of human and mouse methylenetetrahydrofolate reductasas (MTHFR)"*Mammalian Genome*, 1996, pp. 652-656, vol. 9.

Graf, E. et al. "Iron-catalyzed Hydroxyl Radical Formation: Stringent Requirement for Free Iron Coordination Sila"*The Journal of Biological Chemistry*, Mar. 25, 1964, pp. 3620-3624, vol. 259, No. 5.

Granger, D. N. et al. "Role of Oxygen Radicals in the Pathoganesis of Intestinal Ischaria" *The Physiologist*, 1983, pp. 159-164, vol. 25, No. 3.

Grisham, M. B. et al. "Oxident Defense Mechanisms in the Human Colon" *Inflammation*, 1990, pp. 689-880, vol. 14, No. 6.

Gulati, S. et al. "Alterations of peroxisomal function in Iechemia-reperfusion injury of rat kidney" *Blochimica at Blophsica Acte*, 1993, pp. 291-298, vol. 1182, No. 1.

Guyton, A. C. et al. Functional Organization of the Human Body and Control of the 'Internal Environment' to *Human Physiology and Machanisms*, 6th edition, Chapter 1, 1997, p. 3, W. B. Saunders Company.

Han, D. et al. "Manchendrial respiratory chain-dependent generation of superoxide anion and its release into the Intermembrane space"*Biochem, J.,* 2001, pp. 411-416, vol. 353.

Harris, M. L. et al. "Free Radicals and Other Reactive Oxygen, Metabolfites in Inflammatory Bowel Disease: Cause, Consequence or Eplphenomenon!" *Pharmac. Ther.*, 1992, pp. 378-408, vol. 53.

Hendrickson, B. A. et al. "Clinical Aspects and Pathophysiology of Infammatory Bowel Disease" *Clinical Microbiology Reviews*, Jan. 2002, pp. 79-91, vol. 15, No. 1.

Hoek, J. B. et al. "Alcohol and Miochondria: A Dysfunctional Relationship" *Gastroonterology*, 2002, pp. 2049-2063, vol. 122.

Huycke, M. M. et al. "Extraceluler superoxide production by *Enterococcus faecalis* scaiis requires demethylmenaquinone and is attenuated by functional terminal quinol oxidases" *Molecular Microbiology*, 2001, pp. 729-740, vol. 42, No. 3.

Huycke, M. M. et al. "*Enterococcus faecalis* produces extracallular superoxide and hydrogen peroxide that damages colonic epithelal cell DNA". *Carcinogenesis*, 2002, pp. 528-536, vol. 23, No. 3.

Huycke, M. M. et al., "In Vivo Production of Hydroxyl Radical by *Enterococcus faecalis* Colonizing the Intestinal Tract Using Aromatic Hydroxylation" *Free Radical & Medicine*, 2002, pp. 818-828, vol. 33, No. 6.

Isman, C. A. et al. "Methimazole-Induced hypothyroidism in rats smellorates oxidative injury in experimental colitis" *Journal of Endocrinology*, 2003, pp. 471-478, vol. 177.

Jarnerot, G. et al. "The Thyroid in Ulcerative Colitis and Crohn's Disease" *Acta Med. Scand.*, 1975, pp. 83-87, vol. 197.

Karlinger, K. et al. "The epidemiology and the pathogenesis of inflammatory bowel disease" *Eur. J. Radiol.*, Sep. 2000, pp. 154-187, vol. 35, No. 3.

Kawai, M. et al. "A case of ulcerative colitis induced by oral ferrous sulfate" *Acta Paediatr. Jpn.*, Aug. 1992, pp. 476-478, vol. 34, No. 4, abstract only.

Kehrer, J. P. "The Haber-Weiss Reaction and Mechanisms of Toxicity". *Toxicology*, 2000, pp. 43-50, vol. 149.

Keyer, K. et al. "Superoxide accelerates DNA damage by elevating tree-iron levels" *Proc. Natl. Acad. Sci. USA*, Nov. 1996, pp. 13635-13840, vol. 93.

Koutroubakis, I. E. et al. "Hyperhornocysteinemia in Greek Patents with Inflammatory Bowel Disease" *Digestive Diseases and Sciences*, Dec. 2000, pp. 2347-2351, vol. 45, No. 12.

Larsson, A. et al. "Glutathlone Synthetase Deficiency and Other Disorders of the $\gamma$-Glutamyl Cycle" in *The Metabolic& Molecular Bases of Inherited Disease*, 8th edition, Chapter 95, *ed. Scriver et al.*, 2001, pp. 2205-2215, McGraw-Hill Medical Publishing Division.

Lechin, F. et al. "Stress Versus Depression" *Prog. Neuro-Psychophament& Biol. Psychiol*, 1996, pp. 899-950, vol. 20.

Li, C. et al. "Reactive species mechanisms of cellular hypoxie-reoxygenation injury" *Am. J. Physiol. Cell Physid.*, 2002, pp. C227-C241, vol. 282.

Liochev, S. L. et al. "Superoxide and Iron: Partners in Crime" *Life*, 1999, pp. 157-161, vol. 48.

Liu, S-S. "Generating, Partitioning, Targeting and Functioning of superoxide in Mitochondria" *Bioscience Reports*, 1997, pp. 259-272, vol. 17, No. 3.

Madretsma, S. et al. "In-vivo effect of nicotine on cytotone production by human non-adherant mononuclear cells" *Eur. J. Gastroersterol. Hepatol.*, Oct. 1996, pp. 1017-1020, vol. 8, No. 10, abstract only.

Mahmud, N. et al. "Increased prevalence of methylenehetrahydrofolate reductase C677T variant in patients with inflammatory bowel disease and its clinical implications" *Gut*, 1999, pp. 389-394, vol. 45.

Maier, B. R. et al. "Effects of a high-beef diet on bowel flors: a preliminary report" *The America Journal of Clinical Nutrtition*, Dec. 1974, pp. 1470-1474, vol. 27.

"Management of Ulcerative Colitis" National Guideline Clearinghouse: http://www.ngc.gov, 2001, pp. 1-10.

Meyer, C. T. et al. "Hydrogen Peroxide Colitis: A Report of Three Patients" *J. Clin. Gasteroenterol.*, 1981, pp. 31-35, vol. 3.

Meyers, S. et al. "The 'Natural History'of Ulcerative Colitis: An Analysis of the Placebo Response" *J. Clin Gastroentorol.*, 1988, pp. 33-37, vol. 11, No. 1.

Millar, A. D. et al. "Effects of Iron and Iron chaladon In vitro on mucosal oxidant activity in ulcerative colitis" *Aliment Pharmacol, Ther.*, 2000, pp. 1163-1168, vol. 14.

*Mitochondria in Pathocoenesis*, ed. by Lemasters, J. et al, 2001, pp. 281-284, 288, Kluwer Academic/Phenum Publishers.

The Metabolic & Molecular Bases of Inherited Disease, 8th edition, Chapter 155, *eds. Scriver, C. R. et al.*, 2001, pp. 3367-3383, vol. 3, McGraw-Hill Medical Publishing Division.

The Metabolic & Molecular Bases of Inherited Disease, 8th edition, Chapter 102, *eds. Scriver, C. R. et al.*, 2001, pp. 4050-4651, McGraw-Hill Medical Publishing Division.

Modebe, O. "Autolmmune thyroid disease with ulcerative colitis" *Postgraduate Medical Journal*, 1988, pp. 475-478, vol. 62.

Nelson, M. S. "Biochemical and Genetic Characterization of the Lowell Variant. A New Phanotype of 8-Phosphcgluconate Dehydrogenase" *Human Genetics*, 1982, pp. 333-336, vol. 62.

"Nicotine Pharmacology" in *Clearing the Smoke: Assessing the Science Base for Tobacco Hann Reduction*, Chapter 8, 2001, pp. 243, 267.

Odes, H. S. et al. "Effects of Current Cigarette Smoking on Clinical Course of Crohn's Disease and Ulcerative Colitis" *Digestive Diseases and Sciences*, Aug. 2001, pp. 1717-1721, vol. 46, No. 8.

O'Donnell, V. B. et al. "High rates of extracellular superoxide generation by cultured human fibrobissts: involvement of a lipid-metaboixing enzyme" *Biochem, J.* 1996, pp. 805-812, vol. 318.

Oren, R. et al. "Anti-thyroid drugs decrease nucceal damages in a rat model of experimental colitis" *Alimont Pharmacol Thot.*, 1997, pp. 341-345, vol. 11, No. 2.

Outinen, P.A. et al. "Homocystelne-Induced Endoplesnlc Reticulum Stress and Growth Arrest Leads to Specific Changes in Gene Expression in Human Vascular Endothelial Cells" *Blood*, Aug. 1, 1999, pp. 959-967.

Ouyang, Y. et al. "Suppression of human IL-1B, II-2, 1FN-$\gamma$ and TNF$\alpha$ a production by cigarette smoke extracts" *J. Allergy Clin. Immunology*, 2000, pp. 280-287, vol. 108, No. 2.

Owen, R. W. et al. "Generation of reactive oxygen species by the faecal matrix" *Gut.* 2000, pp. 225-232, vol. 46.

Parks, D. A. et al. "Oxygen radicals effects on Intestinal vascular permability" *Gastrointest. Liver Physiol.*, 1984, pp. G157-G170, vol. 10.

Parks, D. A. et al. "Contributions of ischemia and reperfusion to mucosal lesion formation" *Gastrointest, Liver Physiol.*, 1986, pp. G749-G753, vol. 13.

Parr, C. W. "Erythrocyte Phosphogluconate Dehydroganss Polymorphism" *Nature*, Apr. 30, 1966, pp. 487-489, vol. 210, No. 5035.

(56) References Cited

OTHER PUBLICATIONS

Parr, C. W. et al. "Inherited quantitative variations of human phosphogluconate dehydrogenase" *Ann. Hum. Genet.*, 1967, pp. 338-352, vol. 30, No. 4.

Pryor, W. A. et al. "The Inhibitory Effect of Extracts of Cigarette Tax on Election Transport of Mitochondria and Submitochondrial Particles" *Free Radical Biology and Medicine*, 1992, pp. 355-372, vol. 12.

Pumphrey, R. E. "Hydrogen Peroxide Proctitis" *American Journal of Surgery*, Jan. 1951, pp. 60-62, vol. 81.

Rady, P.L. et al. "Methylenetetrahydrofolate reductase (MTHFR): The incidence of Mutations C677T and A1298C in the Ashkenazi Jewish Population" *American Journal of Medical Genetics*, 1998, pp. 380-384, vol. 86, No. 4.

Rao, S. S. C. et al. "Symptoms and stool patterns in potions with ulcerative colitis" *Gut*, 1988, pp. 342-345, vol. 29.

Reifen, R. et al. "Iron Supplementation May Aggrevate Inflammatory Status of Colitis in a Rat Model" *Digestive Diseases and Sciences*, Feb. 2000, pp. 384-397, vol. 43, No. 2.

Ringstad, J. et al. "Seaun Selenium, Copper, and Zinc Concentrations in Crohn's Disease and Ulcerative Colitis" *Scand J. Gasteroenterol.*, 1993, pp. 605-608, vol. 28, No. 7.

Roediger, W. et al. "Metabolic Induction of expermental ulcerative colitis by inhibition of fatty acid coddation" *Br. J. exp. Pathology*, 1988, pp. 773-782, vol. 87.

Roediger, W. et al. "Human Colonocyte Detoxification" *Gut*, 1997, pp. 731-734, vol. 41, No. 8.

Roth, M-P. et al. "Geographic Origins of Jewish Patients With Inflammatory Bowel Disease" *Gastroenterology*, 1989, pp. 900-904, vol. 97, No. 4.

Schultz, B. E., et al. "Structures and Proton-Pumping Strategies of Mitochondrion Respiratory Enzymes" *Annu. Rev. Biophys. Biomol Struct.*, 2001, pp. 23-65, vol. 30.

Schwartz, E. et al. "Letter to the editor, Hydrogen Peroxide Injury to the Colon" *Digestive Diseases and Sciences*, Jun. 1995, pp. 1290-1291, vol. 40, No. 6.

Shaw, A. et al. "Gas Embolism Produced by Hydrogen Peroxide" *The New England Journal of Medicine*, Aug. 3, 1967, pp. 238-241, vol. 277, No. 5.

Sheehan, J.F. et al. "Ulcerative Colitis Following Hydrogen Peroxide Enema: Case Report and Experimental Production with Transient Emphysema of Colonic Wall and Gas Embolism" *Laboratory Investigation*, 1960, pp. 150-168, vol. 9, No. 1.

Soderholm, J. D. et al. "Chronic Stress Induces Mast Cell-Dependent Bacteria Adherence and Initiates Mucosal Inflammation in Rat Intestine" *Gastroenterology*, 2002, pp. 1099-1106, vol. 128.

Soderholm, J. D. et al. "Stress and the Gastrointestinal Tract II. Stress and Intestinal barrier function" *Am. J. Physiol, Gastrointest Liver Physiol.*, 2001, pp. G7-G13, vol. 280.

Souchard, J.P. et al. "Electron spin resonance detection of extracellular superoxide anton releases by cultured endothelial cells" *Free Radio. Res.* Nov. 1996, pp. 441-449, vol. 29, No. 5, abstract only.

Srigiridhar, K. et al. "Oral repletion of Iron Induces free radical mediaind alterations in the gastrointestinal tract of rat" *Molecular and Cellular Biochemistry*, 2001, pp. 91-98, vol. 219, Nos. 1-2.

St-Pierre, J. et al. "Topology of Superoxide Production from Different Sites in the Mitochondrial Electron Transport Chain" *The Journal of Biological Chemistry*, Nov. 22, 2002, pp. 44784-44790, vol. 277, No. 47.

Thibaud, D. et al. "Rectal bleeding: complication of hydrogen peroxide enemas" *Archives de peolistras: organe official de la Sociate française de pidlatrie*, 2001, pp. 1267-1268, vol. 8, No. 11.

Tomlinson, J.E. et al. "Repression of Pentose Phosphate Pathway Dehyogenase Synthests and mRNA by Dietary Fat in Rats" *American Institute of Nutrition*, 1968, pp. 408-415, vol. 118, No. 3.

Topping, D. L. et al. "Short-Chain Fatty Acids and Human Colonic Function: Roles of Resistant Starch and Nonstartch Polycinarides" *Physioiogical Reviews*, Jul. 2001, pp. 1031-1084, vol. 81, No. 3.

Torisu, T. et al. "A Rare Case of Ulcerative Colitis Complicating Wilson's Disease. Possible Association between the Two Diseases" *J. Clin Gastroenatrol.*, 2002, pp. 43-45, vol. 35, No. 1.

Turrens, J. F. "Superoxide Production by the Mitochundrial Respiratory Chain" *Bioscience Reports*, 1997, pp. 3-8, vol. 17, No. 1.

Upchurch, G. R. et al. "Homocyat(e)ine Decreases Bioavailable Nitric Oxide by a Mechanism Involving Glutathione Peroxide" *The Journal of Biological Chemistry*, Jul. 4, 1997, pp. 17012-17017, vol. 272, No. 27.

Van Vleet, T. R. et al. "Inhibition of Human Cylochrome P450 2E1 by Nicotine, Colinine, and Aqueous Cigarette Tax Extract In Vitro" *Toxicological Sciences*, 2001, pp. 185-191, vol. 64.

Venditti, P. et al. "Effects of Thyroid State on $H_2O$ Production by Rat Heart Mlochondria: Sites of Production with Complex I- and Complex II-Linked Substrates" *Hormone Metabolic Research*, 2003, pp. 56-61, vol. 35.

Venditti, P. et al. "Effect of thyroid state on lipid peroxidation antidoxtidant deferenes and susceptibility to oxidateve stress in rat tissues" *Journal of Endocinology*, 1997, pp. 151-157, vol. 156.

Whelan, G. "Epidemiology of Inflammatory Bowel Diseases" *Medical Clinics of North America*, Jan. 1990, pp. 1-12, vol. 74, No. 1.

Wilcken, D. E. L. et al. "Relationship Between Homocysteine and Superoxide Dismutase in Homocyastinuria—Possible Relevance to Cardiovascular Risk" *Arterocular Thromb Vasc., Biol*, May 2000, pp. 1199-1202, vol. 20.

Babior, B. M. et al. "The $O_2$ Producing Enzyme of Human Neutrophlis" *Journal of Biological Chemistry*, Mar. 10, 1981, pp. 2321-2323, vol. 258, No. 5.

Rosenblatt, D. S. "Inherited Disorders of Folate and Cobhlaith Transport and Metabolism" in *The Metabolic & Molecular Bases of Inherited Disease*, 8th edition, Chapter 155, eds Scitver C. R. et. al., 1995, pp. 3897-3910 and 3924-3933, McGraw-Hill Medical Publishing Division.

STN accession number 94: 19078 Kondracki Dissertation Abstracts International, 1993, 53(128) pp. 6206.

Van den Worm, E. "Investigation on apocynin, a potent NADPH oxidase Inhibitor" May 2001, title page and p. 75.

Pfaff, P., Weide, F., and Kuhn R., "Investigation of Derivathalon of Oligosseeharicas by Means of Reductive Amination for Separateion in Capillary Electrophoresis" Chrometographic, Jun. 12, 1999, pp. 536-670, vol. 48, No. 11/12.

Doussiere, J., and Vignais, P.V., "Diphanylana loclonium as an inhibitor of the NADPH coidase complex of bovine neutrophils" *Eut. J. Biochem*, 1992, pp. 61-71, vol. 208.

Kowaltowski, A. J. et al. "Reactive Oxygen Generation by Mitochondria" in *Mitochondris in Eachogamosle* 2001, Chapter 14, eds. Lozaazero et al. et al., pp. 283-285, Eluwer Academic/Plamin Publishers.

R H Grace, A E Gent, and M D Hellier, "Comparative trial of sodium cromogylcate enemas with prednisolone enemas in the treatment of ulcerative colitis", *Gut*, 1987, 28, 88-92.

Scheppach et al., "Effect of Butyrate Enemas on the Colonic Mucosa in Distal Ulcerative Colitis", *Gastroenterology* 1992; 103: 51-56.

Examination Report issued in New Zealand Patent Application No. 581,710 and dated Oct. 29, 2010.

Extended European Search Report issued in European Patent Application No. 11179459.0 and dated Oct. 21, 2011.

Shah S A, et al "A Comparative Review of Topical Therapies for inflammatory Bowel Disease", Clinical Immunotherapeutics, ADIS International, Aukland, NZ, 1996; vol. 6, No. 2.

Vernia P, et al. "Topical Treatment of Refractor Distal Ulcerative Colitis with 5-ASA and Sodium Butyrate" *Digestive Diseases and Sciences*, vol. 40, No. 2 1995, p. 305-307.

The Merck Index 17th edition (1999), p. 302, 307.

Otley, et al. Cochrane Databese Syst. Rev., (Oct. 2005), 19(4): CD000296.

Kolgazi, et al. Journal Gastroenterology Hepatology, (Nov. 2007), 22 (11), p. 159-165 (abstract).

Rintala, et al. Journal of Pediatric Surgery, 36(7) (Jul. 2001), p. 1032-1035.

Gassull, M.A. Alimentary Pharmacology & Therapeutics, (2006), 24 (Suppl. 3), 90-95.

(56) References Cited

OTHER PUBLICATIONS

Babior BM, et al. Journal of Biological Chemistry 1981, 265(5), 2321-2323.

International Search Report and Written Opinion issued in PCT/US2008/007401 and dated Dec. 26, 2008.

Mulder, C. J., et al. Beclomethasone diproplonate (3 mg) versus 5-aminosallcyllc acid (2g) versus the combination of both (3mg/2g) as retention enemas in active ulcerative proctitis. Eur J Gastroenterol Hepatol. 8: 549-553, 1996.

Senagore, A. J., et al. "Short-chain fatty acki enemas,: a cost-effective alternative in the treatment of nonspecific proctosigmoiditis." *Dis Colon Rectum,* 35: 923-927, 1992.

Manguso, F. et al. "Meta-analysis: the efficacy of rectal beclomethasone dipropionate vs. 5-aminosalicylic acid in mild to moderate ulcerative colitis." *Aliment Pharmacol Ther* 26: 21-29, 2007.

International Search Report issued in PCT/US2013/069449 and dated Mar. 17, 2014.

\* cited by examiner

ENEMA COMPOSITION FOR TREATMENT OF ULCERATIVE COLITIS HAVING LONG TERM STABILITY

CROSS-REFERENCE TO RELATED APPLICATION

This patent application claims priority under 35 U.S.C. §119(e) to U.S. Provisional Patent Application No. 61/724,678, filed Nov. 9, 2012, entitled "ENEMA COMPOSITION FOR TREATMENT OF ULCERATIVE COLITIS HAVING LONG TERM STABILITY", the contents of which are incorporated by reference herein in its entirety.

BACKGROUND OF THE INVENTION

Ulcerative colitis (UC) is an inflammatory bowel disease characterized by recurrent bouts of rectal bleeding and bloody diarrhea. The initial inflammatory reaction begins in the rectal mucosa in over 95% of cases and may extend in a contiguous fashion to involve the whole colon. Treatment often involves administration of enemas containing corticosteroids, mesalamine and other ingredients which are useful in the largely palliative care and management of the disease. See, for example, Pravda's U.S. Pat. No. 7,312,243 and US Patent Application Publication No. 2010/0184728, the contents of each of which are incorporated herein by reference.

Multi-component enema products must often be compounded by a pharmacist upon need. Budesonide in a multi-component enema product is prone to oxidation and is, therefore, not suitable for long-term storage in a multi-component enema product. While multi-component enema products have shown promise in advancing therapies for patients with UC, there is an on-going need to provide the therapies in a form which would not only have improved shelf life but also in a format which would enhance patient compliance. The present invention addresses this need.

SUMMARY OF THE INVENTION

In some aspects of the invention, the budesonide-containing solutions include cromolyn sodium, an antioxidizing agent, benzoic acid and a pharmaceutically acceptable fluid including propylene glycol and water. The amount of budesonide included in the compositions is preferably from about 0.1 mg to about 10 mg and the amount of cromolyn sodium included in the compositions is preferably from about 5 mg to about 150 mg. Further aspects of the invention include kits containing a container including the budesonide-containing solutions and one or more separate containers including mesalamine, sodium butyrate, and lipoic acid. Still further aspects of the invention include methods of treatment using the kits.

One of the advantages of the inventive budesonide-containing solutions is that they have substantially improved long term stability. For example, the inventive solutions are substantially free of impurities, i.e. less than 5% total degradants, after about 3 months at a temperature of about 40° C.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

As used herein, RRT is calculated by dividing the retention time of the peak of interest by the retention time of the main peak. Any peak with an RRT <1 elutes before the main peak, and any peak with an RRT >1 elutes after the main peak.

For purposes of the present invention, "substantially free of impurities" shall be understood to include budesonide-containing solutions in which the amount of total impurities is less than about 5%, as calculated on a normalized peak area response ("PAR") basis as determined by high performance liquid chromatography ("HPLC") at a wavelength of 223 nm, after a period of about 3 months at a temperature of 40° C. The amount of impurities is further calculated as being based upon the original amount budesonide being present in the solutions.

For purposes of the present invention, a pharmaceutically acceptable fluid is a fluid which is suitable for pharmaceutical use.

In one aspect of the invention, there are provided long-term stable budesonide-containing solutions including:
a) budesonide or a pharmaceutically acceptable salt thereof;
b) a stabilizing amount of cromolyn or a pharmaceutically acceptable salt or solvate thereof;
c) an antioxidizing agent;
d) a pharmaceutically acceptable organic acid; and
e) a pharmaceutically acceptable fluid including:
   i) propylene glycol; and
   ii) water.

The total degradants in the inventive solutions resulting from the degradation of the budesonide in the compositions is less than about 5% PAR as determined by HPLC at a wavelength of 223 nm after at least about 3 months at a temperature of about 40° C. The 40° C. stability translates into budesonide stability of at least 18 to 30 months under ambient storage conditions. Preferably, the budesonide-containing solutions demonstrate long term storage stability for at least about 2 years, especially when stored at the lower (refrigerated) temperatures. The inventive solutions exhibit less than half total degradants under refrigerated conditions compared to solutions that do not include cromolyn sodium.

In some aspects of the invention, the amount of budesonide in the inventive solutions is from about 0.1 mg to about 10 mg, preferably from about 2.5 mg to about 7.5 mg. It will be understood that solutions containing any useful concentration within the ranges, i.e. 0.5, 1, 2, 3, 4, 5, 6 . . . 10 are contemplated. Preferably, the budesonide amount is about 5 mg. In alternative aspects, the amount of budesonide is outside these ranges, but the amounts will be sufficient for single or multiple administrations of dosages generally regarded as effective amounts. In some aspects of the invention, pharmaceutically acceptable salts of budesonide are also contemplated.

In some aspects of the invention, the cromolyn is cromolyn sodium or cromolyn disodium.

Without meaning to be bound by any theory or hypothesis, the cromolyn sodium can have a stabilizing effect on the budesonide. For purposes of the present invention, "stabilizing amount" shall be understood to include those amounts which increase or enhance the stability of the budesonide in the compositions described herein. The stabilizing amount of cromolyn sodium stabilizes budesonide while also being effective at treating ulcerative colitis. In some aspects of the invention, a stabilizing amount of cromolyn sodium in the budesonide-containing solutions is from about 5 mg to about 150 mg, preferably from about 20 mg to about 125 mg. In other embodiments, the amount of cromolyn sodium is about 33 mg. In other embodiments, the amount of cromolyn sodium is about 70 mg. Preferably, the amount of cromolyn sodium is about 100 mg. In some aspects of the invention, the inventive compositions are substantially free of impurities, i.e. less than 5% total degradants after about 3 months at 40° C. Without meaning to be bound by any theory or hypothesis, less than 5% total degradants for budesonide shall be understood to be a level sufficient to maintain the therapeutic efficacy of budesonide.

The budesonide-containing solutions according to the invention may also include an antioxidizing agent that is pharmaceutically acceptable. For example, the antioxidizing agent can be selected from among bisulfites and their salts, sulfurous acid and salts, ascorbic/iso-ascorbic acid and their salts, thiols and mixtures thereof. Preferably, the antioxidizing agent is potassium metabisulfite. Suitable antioxidizing agent amounts in the inventive solutions can range from about 0.2 mg to about 20 mg, preferably from about 5 mg to about 15 mg. Preferably, the amount of the antioxidizing agent is about 10 mg.

In some aspects of the invention, the budesonide-containing solutions include a pharmaceutically acceptable organic acid, such as benzoic acid, citric acid, lactic acid, sorbic acid and mixtures thereof. Preferably, the organic acid is benzoic acid. The amount of the organic acid in the inventive solutions can be from about 0.2 mg to about 50 mg, and preferably from about 5 mg to about 15 mg, or from about 10 mg to about 20 mg. In some other embodiments, the amount of the organic acid in the budesonide-containing solutions is about 10 mg.

In several aspects of the invention, the pharmaceutically acceptable fluid includes a mixture of propylene glycol (PG) and water. For example, the pharmaceutically acceptable fluid can include about 50% PG and about 50% water. Alternatively, pharmaceutically acceptable fluid includes about 30% PG and about 70% water. The amount of PG and water can also be varied within the ranges, i.e. the ratio of PG:water in the pharmaceutically acceptable fluid can range from about 75:25 to about 30:70. Within this range, is a pharmaceutically acceptable fluid containing about 75% PG and about 25% water, and preferably 50% PG and 50% water.

Further embodiments of the invention include long-term stable budesonide-containing solutions such as those described above and further having the characteristics of

| Ingredient | % by Weight Range | Range per unit dose |
|---|---|---|
| budesonide | about 0.001 to about 0.1 | 0.1 to 10 mg |
| cromolyn sodium | about 0.05 to about 0.2 | 5 to 1000 mg |
| antioxidizing agent | about 0.002 to about 0.2 | 0.2 to 20 mg |
| organic acid | about 0.002 to about 0.2 | 0.2 to 50 mg |
| propylene glycol | about 10 to about 90 | 1 g to 9 g |
| water | about 10 to about 90 | 1 g to 9 g |
| auxiliary ingredients/ excipients | 0 to about 10% | 0 to 1 g |
| total | 100 | 10 g |

Other additives which may be included in the solutions include free radical or metal scavengers such as EDTA and lactobionic acid.

In some aspects of the invention, the amounts of the ingredients of the inventive solutions are provided per unit dose. Preferably, the unit dose volume is from about 5 ml to about 15 ml. In some aspects the unit dose volume is from about 10 ml to about 15 ml. In alternative aspects, the volume is outside these ranges, but the amounts of the ingredients will be sufficient for single or multiple administrations of dosages. Preferably, the unit dose volume is about 10 ml.

The budesonide-containing solutions described herein have advantageously long term stability. For example, the inventive solutions have less than 0.2% total (budesonide) degradants after 3 months at 5° C. The amount of total degradants in the solution after 3 months at 25° C. is less than 0.5%. While the amount of total degradants in the solution after 3 months at 40° C. is less than 5%. These accelerated stability data confirm that the shelf life of the solutions is well in excess of one year or longer when stored at room temperature or when refrigerated.

The invention also includes kits for the treatment of ulcerative colitis. Some preferred kits in accordance with the invention include a plurality of containers suitable for holding pharmaceutically acceptable materials. A first container includes a therapeutically effective amount of the long-term stable budesonide-containing solutions described herein. A second container includes a therapeutically effective amount of mesalamine or pharmaceutically acceptable aminosalicylic acid. In some aspects, the mesalamine is kept at a pH of below about 5.0. In some aspects of the invention, the second container optionally includes sodium butyrate. In other aspects of the invention, the kit includes a third container that includes a therapeutically sufficient amount of sodium butyrate.

According to several preferred aspects of the invention, the container contents are formulated for rectal administration. In some aspects of the invention, the container contents are in a suppository form or an enema solution. Preferably the contents are an enema product. The contents of the containers found in the kit are combined using techniques well known to those of ordinary skill in order to form a product for rectal administration which is ready for administration to a patient in need thereof.

In some preferred aspects of the invention the second vessel includes mesalamine or a pharmaceutically acceptable salt thereof, as well as pharmaceutically acceptable agents including an acidifying agent, an antioxidizing agent, an antimicrobial preservative, free radical scavengers or metal scavengers, a mixture of microcrystalline cellulose (MCC) and carboxymethylcellulose (CMC), and water. In other aspects of the invention, the second vessel also includes sodium butyrate.

The amount of mesalamine or a pharmaceutically acceptable salt thereof typically included in unit doses included in the kits is from about 50 mg to about 5,000 mg, preferably from about 750 mg to about 3000 mg or from about 1500 mg to about 2600 mg. Preferably, the amount of mesalamine or a pharmaceutically acceptable salt thereof included in unit doses included in the second vessel is about 2000 mg.

The acidifying agent can be selected from acetic acid, citric acid, sorbic acid, lactic acid, HCl and phosphoric acid. Preferably, the acidifying agent is citric acid. The amount of the acidifying agent included in unit doses in the kits is from about 75 mg to about 150 mg, and preferably 100 mg.

The antioxidizing agent in the second vessel in the kits can be selected from among bisulfites and their salts, sulfurous acid and salts, ascorbic/iso-ascorbic acid and their salts, thiols and mixtures thereof. Preferably, the antioxidizing agent is potassium metabisulfite. The amount of the antioxidizing agent included in unit doses in the second vessel is from about 40 mg to about 80 mg, and preferably about 60 mg.

The antimicrobial preservative can be selected from benzoic acid and salts, sorbic acid and salts, boric acids and salts, parabens, imidurea, monothioglycerol, pentetic acid, phenyl mercuric borate, phenyl mercuric nitrate, potassium metabisulfite, propionic acid, lactic acids and salts, sodium sulfite, and thimerosol. Preferably, the antimicrobial preservative is sodium benzoate. The amount of the antimicrobial preservative included in unit doses in the kits is from about 150 mg to about 250 mg, and preferably about 180 mg.

The metal scavenger in the second vessel in the kits can be selected from among EDTA and lactobionic acid. Preferably, the metal scavenger is EDTA. The amount of metal scavenger included in unit doses in the second vessel is from about 40 mg to about 70 mg, and preferably about 50 mg.

Some embodiments also include an effective amount of a chain stopper (i.e., a free radical scavenger). Free radical scavengers are selected from BHT, BHA, alpha-tocopherol and its various pharmaceutical forms, propyl gallate and other compounds that are known to scavenge free radicals. The amount of the free radial scavenger is determined by the nature of each compound. For example, BHT and BHA are present in quantities of from about 0.0005% to about 0.3% within the formulation. Alpha-tocopherol are present in quantities of from about 0.001% to 0.05% within the formulation.

The mixture of MCC and CMC in the kits according to several aspects of the invention can be mixtures of MCC and CMC such as the products available under the trade name of AVICEL, i.e. AVICEL RC-591 and AVICEL CL-611. Preferably, the mixture of MCC and CMC is a blend of microcrystalline cellulose and sodium carboxymethylcellulose, such as AVICEL RC-591. The amount of the mixture of MCC and CMC included in unit doses in the kits is from about 500 mg to about 1.5 g, and preferably from about 590 mg to about 1 g. Preferably, the amount of mixture of MCC and CMC is about 590 mg.

The amount of sodium butyrate typically included in unit doses in the kits is from about 5 millimoles to about 50 millimoles, preferably 15 millimoles. In other aspects of the invention, the amount of sodium butyrate is from about 0.56 mg to about 5.55 g, preferably 100 mg to 1700 mg. In some embodiments, the amount is 125 mg. In other embodiments, the amount is 1,665 mg.

In some aspects of the invention, the amounts of the ingredients of the solutions in the second container are provided per unit dose. Preferably, the unit dose volume in the second container is from about 40 ml to about 70 ml. In some aspects the unit dose volume in the second container is from about 50 ml to about 60 ml. In alternative aspects, the volume in the second container is outside these ranges, but the amounts will be sufficient for single or multiple administrations of dosages. Preferably, the unit dose volume in the second container is about 60 ml.

In some aspects of the invention, the amounts of the ingredients of the contents of the third container are provided per unit dose. Preferably, the unit dose volume in the third container is from about 5 ml to about 15 ml. In some aspects the unit dose volume in the third container is about 10 ml. In some aspects of the invention, the contents of the third container are formulated as an enema product. In alternative aspects, the contents of the third container include a suppository. Preferably, the contents of the third container are formulated as an enema product.

In some aspects of the invention, sodium butyrate can be formulated as a separate entity. The sodium butyrate can be formulated as a suppository or an aqueous enema solution. In some embodiments, after rectal administration of an enema product as described herein, a sodium butyrate suppository can be inserted to prevent any leakage of enema. Preferably, the suppository will dissolve in 30 to 45 minutes. In alternative embodiments, an aqueous enema solution of sodium butyrate (1.6 g in 10 ml water) can be added to the combined contents of the first and second containers.

In some aspects of the invention, the kit may also optionally include an effective amount of a lipoic acid provided in a separate container. The lipoic acid is selected from alpha lipoic acid and R-dihydro-lipoic acid. Preferably, the lipoic acid is R-dihydro-lipoic acid. The amount of lipoic acid is provided per unit dose. Preferably, the amount of lipoic acid is from about 100 mg to about 1,000 mg, preferably from about 250 mg to about 750 mg. In some aspects, the amount of lipoic acid is outside these ranges, but the amounts will be sufficient for single or multiple administrations of dosages. Preferably the amount of lipoic acid is 300 mg. The lipoic acid is preferably formulated for oral administration. The contents of the container including lipoic acid found in the kit are prepared using techniques well known to those of ordinary skill in order to form a product for oral administration which is ready for administration to a patient in need thereof.

As will be appreciated by those of ordinary skill, the kits will contain other pharmaceutically necessary materials for storing and/or administering the drug, including instructions for storage and use, additional diluents, if desired, etc.

Another embodiment of the invention provides methods of treating ulcerative colitis. The methods include administering to a patient in need thereof the contents of one of the kits containing the budesonide-containing solutions described herein. The methods include providing to a patient in need thereof one of the kits described herein, subsequently combining the contents of the first, second, and, if present, third containers to form an enema composition, and rectally administering the resulting combination, optionally in combination with oral administration of lipoic acid.

EXAMPLES

Following are examples which illustrate procedures for practicing the invention. These examples should not be construed as limiting. All percentages are by weight and all solvent mixture proportions are by volume unless otherwise noted.

Example 1

Budesonide-containing bulk solutions were prepared as follows:

Formulation A (Comparative) was prepared by combining 75.8 mg of budesonide, 150.2 mg of benzoic acid, and 150.3 mg potassium metabisulfite and mixed. 75 ml of propylene glycol was added and then 75 ml of water for injection was added to the budesonide, benzoic acid and potassium metabisulfite mixture. The mixture was then sonicated for 5-6 minutes to obtain a clear solution. The budesonide-containing solution was then transferred to bottles and capped, with each bottle containing 10 ml. The samples were maintained at 40° C./75% relative humidity (RH), and 25° C./60% RH and 5° C./60% RH and analyzed after 15 days, one month, three months or five months for drug content and impurity profile as indicated in Table 1. The results obtained are presented in Table 1.

Formulation B (Inventive) was prepared by combining 75.7 mg of budesonide, 521.1 mg of cromolyn sodium, 150 mg of benzoic acid, and 150.5 mg potassium metabisulfite and mixed. 75 ml of propylene glycol was added and then 75 ml of water for injection was added to the budesonide, cromolyn sodium, benzoic acid and potassium metabisulfite mixture. The mixture was then sonicated for 5-6 minutes to obtain a clear solution. The budesonide-containing solution was then transferred to bottles and capped, with each bottle containing 10 ml. The samples were maintained at 40° C./75% RH, and 25° C./60% RH and 5° C./60% RH and analyzed after 15 days, one month, three months or five months for drug content and impurity profile as indicated in Table 1. The results obtained are presented in Table 1.

Formulation C (Inventive) was prepared by combining 75.71 mg of budesonide, 1.1 g of cromolyn sodium, 150 mg of benzoic acid, and 150.2 mg potassium metabisulfite and mixed. 75 ml of propylene glycol was added and then 75 ml of water for injection was added to the budesonide, cromolyn sodium, benzoic acid and potassium metabisulfite mixture. The mixture was then sonicated for 5-6 minutes to obtain a clear solution. The budesonide-containing solution was then transferred to bottles and capped, with each bottle containing 10 ml. The samples were maintained at 40° C./75% RH, and 25° C./60% RH and 5° C./60% RH and analyzed after 15 days, one month, three months or five months for drug content and impurity profile as indicated in Table 1. The results obtained are presented in Table 1.

Formulation D (Inventive) was prepared by combining 75.73 mg of budesonide, 1.578 g of cromolyn sodium, 150.1 mg of benzoic acid, and 150 mg potassium metabisulfite and mixed. 75 ml of propylene glycol was added and then 75 ml of water for injection was added to the budesonide, cromolyn sodium, benzoic acid and potassium metabisulfite mixture. The mixture was then sonicated for 5-6 minutes to obtain a clear solution. The budesonide-containing solution was then transferred to bottles and capped, with each bottle containing 10 ml. The samples were maintained at 40° C./75% RH, and 25° C./60% RH and 5° C./60% RH and analyzed after 15 days, one month, or three months for budesonide content and impurity profile as indicated in Table 1 and cromolyn sodium content as indicated in Table 2. The results obtained are presented in Table 1 and Table 2.

TABLE 1

Stability of Budesonide

| Formulation | Temp | Time period | Content (mg/mL) | % of Initial | % total degradants | Remarks |
|---|---|---|---|---|---|---|
| Formulation A | Initial | 0 | 0.51 | 100.0 | 0.00 | Clear colorless solution |
| (Comparative) | 40° C. | 15 D | 0.48 | 94.1 | 3.02 | Clear colorless solution |
| Budesonide-5 mg | | 1 M | 0.45 | 88.2 | 7.54 | Clear colorless solution |
| Benzoic acid-10 mg | | 3 M | 0.24 | 47.1 | 14.8 | Clear colorless solution |
| Potassium | 25° C. | 15 D | 0.50 | 98.0 | 1.81 | Clear colorless solution |
| metabisulfite-10 mg | | 1 M | 0.48 | 94.1 | 2.30 | Clear colorless solution |
| Propylene glycol- | | 3 M | 0.46 | 90.2 | 3.95 | Clear colorless solution |
| 5 mL | 5° C. | 15 D | 0.52 | 102.0 | 0.28 | Clear colorless solution |
| WFI qs 5 mL | | 1 M | 0.52 | 102.0 | 0.40 | Clear colorless solution |
| | | 3 M | 0.52 | 102.0 | 0.45 | Clear colorless solution |
| Formulation B | Initial | 0 | 0.53 | 100.0 | Not detected | Clear colorless solution |
| Budesonide-5 mg | | | | | | |
| Cromolyn sodium- | 40° C. | 15 D | 0.52 | 98.1 | 0.15 | Clear colorless solution |
| 33 mg | | 1 M | 0.52 | 98.1 | 0.06 | Clear colorless solution |
| Benzoic acid-10 mg | | 3 M | 0.52 | 98.1 | 0.06 | Clear colorless solution |
| Potassium | 25° C. | 15 D | 0.52 | 98.1 | 0.15 | Clear colorless solution |
| metabisulfite-10 mg | 5° C. | 15 D | 0.52 | 98.1 | 0.15 | Clear colorless solution |
| Propylene glycol- | | | | | | |
| 5 mL | | | | | | |
| WFI qs 5 mL | | | | | | |
| Formulation C | Initial | 0 | 0.51 | 100.0 | Not detected | Clear colorless solution |
| Budesonide-5 mg | | | | | | |
| Cromolyn sodium- | 40° C. | 15 D | 0.51 | 100.0 | 0.14 | Clear colorless solution |
| 66 mg | | 1 M | 0.50 | 98.0 | 0.27 | Clear colorless solution |
| Benzoic acid-10 mg | | 3 M | 0.51 | 100 | 0.08 | Clear colorless solution |
| Potassium | 25° C. | 15 D | 0.51 | 100.0 | 0.00 | Clear colorless solution |
| metabisulfite-10 mg | 5° C. | 15 D | 0.51 | 100.0 | 0.00 | Clear colorless solution |
| Propylene glycol- | | | | | | |
| 5 mL | | | | | | |
| WFI qs 5 mL | | | | | | |
| Formulation D | Initial | 0 | 0.50 | 100 | Not detected | Clear colorless solution |
| Budesonide-5 mg | | | | | | |
| Cromolyn sodium- | 40° C. | 15 D | 0.50 | 100 | 0.10 | Clear colorless solution |
| 100 mg | | 1 M | 0.50 | 100 | 0.43 | Clear colorless solution |
| Benzoic acid-10 mg | | 3 M | 0.48 | 96.0 | 3.87 | Clear colorless solution |
| Potassium | 25° C. | 15 D | 0.50 | 100 | 0.00 | Clear colorless solution |
| metabisulfite-10 mg | 5° C. | 15 D | 0.50 | 100 | 0.00 | Clear colorless solution |
| Propylene glycol- | | | | | | |
| 5 mL | | | | | | |
| WFI qs 5 mL | | | | | | |

TABLE 2

Stability of Cromolyn Sodium

| Formulation | Temp | Time period | Content (mg/mL) | % of Initial |
|---|---|---|---|---|
| Formulation B | | | | |
| Budesonide-5 mg | Initial | 0 | 3.27 | 100 |
| Cromolyn sodium- | 40° C. | 15 D | 3.25 | 99.4 |
| 33 mg | | 1 M | 3.27 | 100 |
| Benzoic acid- | | 3 M | 3.29 | 100.6 |
| 10 mg | 25° C. | 15 D | 3.22 | 98.5 |
| Potassium | 5° C. | 15 D | 3.31 | 101.2 |
| metabisulfite- | | | | |
| 10 mg | | | | |
| Propylene glycol- | | | | |
| 5 mL | | | | |
| WFI qs 5 mL | | | | |
| Formulation C | | | | |
| Budesonide-5 mg | Initial | 0 | 6.46 | 100.0 |
| Cromolyn sodium- | 40° C. | 15 D | 6.19 | 95.8 |
| 66 mg | | 1 M | 6.34 | 98.1 |

TABLE 2-continued

Stability of Cromolyn Sodium

| Formulation | Temp | Time period | Content (mg/mL) | % of Initial |
|---|---|---|---|---|
| Benzoic acid-10 mg | | 3 M | 6.34 | 98.1 |
| Potassium metabisulfite-10 mg | 25° C. | 15 D | 6.37 | 98.6 |
| Propylene glycol-5 mL | 5° C. | 15 D | 6.46 | 100.0 |
| WFI qs 5 mL | | | | |
| Formulation D | | | | |
| Budesonide-5 mg | Initial | 0 | 9.7 | 100 |
| Cromolyn sodium-100 mg | 40° C. | 15 D | 9.52 | 98.1 |
| | | 1 M | 9.80 | 101.0 |
| Benzoic acid-10 mg | | 3 M | 9.67 | 99.7 |
| | 25° C. | 15 D | 9.63 | 99.3 |
| Potassium metabisulfite-10 mg | 5° C. | 15 D | 9.88 | 101.9 |
| Propylene glycol-5 mL | | | | |
| WFI qs 5 mL | | | | |

As shown in Table 1, the inventive budesonide-containing solutions are very stable in solutions containing cromolyn sodium. Table 1 shows that solutions containing budesonide in the presence of from 5 mg to 150 mg cromolyn sodium, had less than about 5% total degradants due to the degradation of budesonide after 3 months storage at 40° C. Even at refrigerated conditions, i.e. 5° C., the inventive solutions demonstrate a 50% or better improvement over the comparative sample. The data presented in Table 2 shows that cromolyn sodium is also stable after 3 months storage at 40° C.

The data presented in Tables 1 and 2 translates to budesonide-containing solutions including 5 mg to 150 mg cromolyn sodium having a shelf life of at least about 18 months at ambient storage conditions. In fact, the inventive compositions are expected to be stable for at least 30 months under ambient storage conditions with much lower degradation than the comparative sample. In contrast, the sample which did not contain cromolyn sodium exhibited more than 14% total degradants under the same storage conditions. Such solutions would not be suitable for long-term storage as described herein.

Example 2

Formulation E (Inventive) was prepared in the same manner as Formulation D in Example 1 above. The samples were maintained at 25° C./60% RH and 5° C./60% RH and analyzed after 15 days, one month, or three months for budesonide content and impurity profile as indicated in Table 3. The results obtained are presented in Table 3.

TABLE 3

Stability of Budesonide

| Formulation E | Temp | Time period | Content (mg/mL) | % of Initial | % of total degradants |
|---|---|---|---|---|---|
| Budesonide-5 mg | | | Budesonide | | |
| Cromolyn sodium-100 mg | | Initial | 0.52 | 100.0 | |
| | 25° C. | 15 D | 0.53 | 101.5 | |
| Benzoic Acid-10 mg | | 1 M | 0.53 | 101.9 | |
| Potassium | | 3 M | 0.53 | 101.9 | 0.31 |
| metabisulfite-10 mg | 5° C. | 15 D | 0.53 | 101.7 | |

TABLE 3-continued

Stability of Budesonide

| Formulation E | Temp | Time period | Content (mg/mL) | % of Initial | % of total degradants |
|---|---|---|---|---|---|
| Propylene glycol-5 mL | | 1 M | 0.53 | 101.9 | |
| WFI-5 mL | | 3 M | 0.53 | 101.9 | 0.00 |

As shown in the table, less than about 0.5% potency loss of budesonide was observed when stored at 25° C. for 3 months. These data suggest that solutions containing budesonide in the presence of from 5 mg to 150 mg cromolyn sodium are stable for at least 18 to 30 months under ambient storage conditions. Disodium cromolyn is not a recognized stabilizing agent. However, it was found that the improved stability of budesonide in the presence of disodium cromolyn is unexpected.

Example 3

Mesalamine-containing bulk compositions were prepared as follows:

Formulation F (Inventive) was prepared by adding 2.61 g sodium benzoate to 500 ml water for injection and mixing for about 5 minutes. 0.84 g potassium metabisulfite was added to the sodium benzoate composition and mixed for about 5 minutes. 14.5 g of AVICEL RC-591 was added to the sodium benzoate and potassium metabisulfite composition and mixed for about 15 minutes. 29.89 g of mesalamine was added to the sodium benzoate, potassium metabisulfite, and AVICEL RC-591 composition. The composition was mixed for about 15 minutes and the pH of the mixture was 5.25. 1.45 g of citric acid was then added to the composition and mixed for about 5 minutes. 0.725 g of EDTA was added, and the resultant composition was mixed from about 5 minutes. The pH of the composition was 4.25. Subsequently, 1.83 g of sodium butyrate was added to the composition and mixed for about 20 minutes. The pH of the composition was 4.45. The resultant composition was then transferred to 40 cc bottles and sealed, with each bottle containing 10 ml. The samples were maintained at 40° C./75% RH, and 25° C./60% RH and 5° C./60% RH and analyzed after 15 days, one month, three months or five months for drug content and impurity profile as indicated in Table 4. The results obtained are presented in Table 4.

Formulation G (Inventive) was prepared by adding 2.61 g sodium benzoate to 500 ml water for injection and mixing for about 5 minutes. 840.3 mg potassium metabisulfite was added to the sodium benzoate composition and mixed for about 5 minutes. 14.45 g of AVICEL RC-591 was added to the sodium benzoate and potassium metabisulfite composition and mixed for about 30 minutes. 29.94 g of mesalamine was added to the sodium benzoate, potassium metabisulfite, and AVICEL RC-591 composition. The composition was mixed for about 15 minutes and the pH of the mixture was 5.24. 1.44 g of citric acid was then added to the composition and mixed for about 5 minutes. 720.5 mg of EDTA was added, and the resultant composition was mixed from about 5 minutes. The pH of the composition was 4.24. Subsequently, 1.83 g of sodium butyrate was added to the composition and mixed for about 20 minutes. The pH of the composition was 4.50. The resultant composition was then transferred to 40 cc bottles and sealed, with each bottle containing 10 ml. The samples were maintained at 40° C./75% RH, and 25° C./60% RH and 5° C./60% RH and analyzed after 7 days, 14 days, one month or three months for drug content and impurity profile as indicated in Table 4. The results obtained are presented in Table 4.

TABLE 4

Stability of Mesalamine and Sodium Butyrate

| | Temp | Time period | Content (mg/mL) | % of Initial | % total degradants |
|---|---|---|---|---|---|
| Formulation F | | | Mesalamine | | |
| Mesalamine-2.08 g | Initial | | 41.1 | 100 | 0.00 |
| Sodium butyrate-125 mg | 40° C. | 7 D | 28.4 | 69.2 | 0.21 |
| | | 14 D | 57.5 | 140.1 | 0.14 |
| Citric acid anydrous-100 mg | 25° C. | 7 D | 27.0 | 65.8 | 0.07 |
| | | 14 D | 70.9 | 172.7 | 0.00 |
| Potassium | | | Sodium Butyrate | | |
| metabisulfite-58.3 mg | Initial | | 2.58 | 100 | Not detected |
| Sodium benzoate-180 mg | 40° C. | 7 D | 2.56 | 99.2 | |
| EDTA-50 mg | 25° C. | 7 D | 2.56 | 99.2 | |
| AVICEL RC 591-1 g | | | | | |
| WFI qs 50 mL | | | | | |
| Formulation G | | | Mesalamine | | |
| Mesalamine-2.08 g | Initial | | 41.8 | 100 | 0.00 |
| Sodium butyrate-125 mg | 40° C. | 1 M | 41.6 | 99.5 | 0.21 |
| | | 2 M | 41.5 | 99.3 | 0.27 |
| Citric acid anydrous-100 mg | | 3 M | 41.4 | 99.0 | 0.96 |
| Potassium | | | Sodium Butyrate | | |
| metabisulfite-58.3 mg | Initial | | 2.49 | 100 | Not detected |
| Sodium benzoate-180 mg | 40° C. | 1 M | 2.49 | 100 | |
| EDTA-50 mg | | 2 M | 2.49 | 100 | |
| AVICEL RC 591-1 g | | 3 M | 2.45 | 98.4 | |
| WFI qs 50 mL | | | | | |

As shown in Table 4, the compositions containing mesalamine and sodium butyrate are very stable. Table 4 shows that compositions containing mesalamine and sodium butyrate had less than about 1% total degradants due to the degradation of mesalamine after 3 months storage at 40° C. The data presented in Table 4 also shows that cromolyn sodium is stable after 3 months storage at 40° C. The data presented in Table 4 translates to compositions containing mesalamine and sodium butyrate having a shelf life of at least about 18 months at ambient storage conditions.

What is claimed is:

1. A long-term stable budesonide-containing solution, comprising
   a) from about 0.1 mg to about 10 mg budesonide or a pharmaceutically acceptable salt thereof;
   b) from about 5 mg to about 150 mg cromolyn or a pharmaceutically acceptable salt or solvate thereof;
   c) from about 5 mg to about 25 mg of an antioxidizing agent;
   d) from about 5 mg to about 50 mg benzoic acid; and
   e) a pharmaceutically acceptable fluid comprising:
      i) from about 20% (v/v) to about 90% (v/v) propylene glycol; and
      ii) water.

2. The long-term stable budesonide-containing solution of claim 1, wherein the amount of the budesonide is from about 2.5 mg to about 7.5 mg.

3. The long-term stable budesonide-containing solution of claim 2, wherein the amount of the budesonide is about 5 mg.

4. The long-term stable budesonide-containing solution of claim 1, wherein the cromolyn is cromolyn sodium in an amount of from about 30 mg to about 125 mg.

5. The long-term stable budesonide-containing solution of claim 4, wherein the amount of the cromolyn sodium is about 100 mg.

6. The long-term stable budesonide-containing solution of claim 1, wherein the antioxidizing agent is selected from the group consisting of potassium metabisulfite, sodium metabisulfite, sulfurous acid, ascorbic/iso-ascorbic acid and their salts, thiols and mixtures thereof.

7. The long-term stable budesonide-containing solution of claim 6, wherein the antioxidizing agent is potassium metabisulfite.

8. The long-term stable budesonide-containing solution of claim 1, wherein the amount of the antioxidzing agent is from about 0.2 mg to about 20 mg.

9. The long-term stable budesonide-containing solution of claim 8, wherein the amount of the antioxidzing agent is about 10 mg.

10. The long-term stable budesonide-containing solution of claim 1, wherein the amount of benzoic acid is from about 0.2 mg to about 50 mg.

11. The long-term stable budesonide-containing solution of claim 10, wherein the amount of benzoic acid is about 10 mg.

12. The long-term stable budesonide-containing solution of claim 1, wherein the pharmaceutically acceptable fluid comprises from about 30% (v/v) to about 75% (v/v) propylene glycol.

13. The long-term stable budesonide-containing solution of claim 12, wherein the pharmaceutically acceptable fluid comprises about 50% (v/v) propylene glycol.

14. The long-term stable budesonide-containing solution of claim 1, further comprising a free radical scavenger or metal scavenger.

15. The long-term stable budesonide-containing solution of claim 14, wherein the metal scavenger is selected from the group consisting of EDTA and lactobionic acid.

16. The long-term stable budesonide-containing solution of claim 1, wherein the total volume of the solution is from about 5 ml to about 15 ml.

17. The long-term stable budesonide-containing solution of claim 16, wherein the total volume of the solution is about 10 ml.

18. A long-term stable budesonide-containing solution, comprising
   a) about 5 mg budesonide or a pharmaceutically acceptable salt thereof;
   b) about 100 mg cromolyn sodium;
   c) about 10 mg potassium metabisulfite;
   d) about 10 mg benzoic acid; and
   e) a pharmaceutically acceptable fluid comprising:
      i) about 50% (v/v) propylene glycol; and
      ii) water.

19. A long-term stable budesonide-containing solution of claim 1, wherein the amount of total degradants in the solution after 3 months at 40° C. is less than 5%.

20. A kit for the treatment of ulcerative colitis, comprising:
   a) a first container comprising a therapeutically effective of amount of the long-term stable budesonide-containing solution of claim 1; and
   b) a second container comprising:
      i) from about 50 mg to about 5,000 mg mesalamine or a pharmaceutically acceptable salt thereof;
      ii) from about 5 millimoles to about 50 millimoles sodium butyrate;
      iii) from about 75 mg to about 150 mg citric acid;
      iv) from about 40 mg to about 80 mg potassium metabisulfite;
      v) from about 150 mg to about 250 mg sodium benzoate;
      vi) from about 40 mg to about 70 mg EDTA;

vii) from about 500 mg to about 1.5 g of a mixture of microcrystalline cellulose and carboxymethylcellulose; and viii) water.

21. A kit for the treatment of ulcerative colitis, comprising:
a) a first container comprising a therapeutically effective of amount of the long-term stable budesonide-containing solution of claim 1;
b) a second container comprising:
  i) from about 50 mg to about 5,000 mg mesalamine or a pharmaceutically acceptable salt thereof;
  ii) from about 5 millimoles to about 50 millimoles sodium butyrate;
  iii) from about 75 mg to about 150 mg citric acid;
  iv) from about 40 mg to about 80 mg potassium metabisulfite;
  v) from about 150 mg to about 250 mg sodium benzoate;
  vi) from about 40 mg to about 70 mg EDTA;
  vii) from about 500 mg to about 1.5 g of a mixture of microcrystalline cellulose and carboxymethylcellulose; and
  viii) water; and
c) a third container comprising from about 100 mg to about 1,000 mg lipoic acid.

22. The kit of claim 21, wherein the lipoic acid is alpha lipoic acid or R-dihydro-lipoic acid.

23. A kit for the treatment of ulcerative colitis, comprising:
a) a first container comprising a therapeutically effective of amount of the long-term stable budesonide-containing solution of claim 1,
b) a second container comprising:
  i) from about 50 mg to about 5,000 mg mesalamine or a pharmaceutically acceptable salt thereof;
  ii) from about 75 mg to about 150 mg citric acid;
  iii) from about 40 mg to about 80 mg potassium metabisulfite;
  iv) from about 150 mg to about 250 mg sodium benzoate;
  v) from about 40 mg to about 70 mg EDTA;
  vi) from about 500 mg to about 1.5 g of a mixture of microcrystalline cellulose and carboxymethylcellulose; and
  vii) water; and
c) a third container comprising;
  i) from about 5 millimoles to about 50 millimoles sodium butyrate; and
  ii) water.

24. A kit for the treatment of ulcerative colitis, comprising:
a) a first container comprising a therapeutically effective of amount of the long-term stable budesonide-containing solution of claim 1,
b) a second container comprising:
  i) from about 50 mg to about 5,000 mg mesalamine or a pharmaceutically acceptable salt thereof;
  ii) from about 75 mg to about 150 mg citric acid;
  iii) from about 40 mg to about 80 mg potassium metabisulfite;
  iv) from about 150 mg to about 250 mg sodium benzoate;
  v) from about 40 mg to about 70 mg EDTA;
  vi) from about 500 mg to about 1.5 g of a mixture of microcrystalline cellulose and carboxymethylcellulose; and
  vii) water;
c) a third container comprising;
  i) from about 5 millimoles to about 50 millimoles sodium butyrate; and
  ii) water; and
d) a fourth container comprising from about 100 mg to about 1,000 mg lipoic acid.

25. The kit of claim 24, wherein the lipoic acid is alpha lipoic acid or R-dihydro-lipoic acid.

26. A method of treating ulcerative colitis in a patient requiring such treatment, comprising:
a) providing the kit of claim 20;
b) combining the contents of the first and second containers; and
c) rectally administering the resulting combination of step b).

27. A method of treating ulcerative colitis in a patient requiring such treatment, comprising:
a) providing the kit of claim 21;
b) combining the contents of the first and second containers;
c) rectally administering the resulting combination of step b); and
d) orally administering the lipoic acid of the third container.

28. A method of treating ulcerative colitis in a patient requiring such treatment, comprising:
a) providing the kit of claim 23;
b) combining the contents of the first, second, and third containers;
c) rectally administering the resulting combination of step b).

29. A method of treating ulcerative colitis in a patient requiring such treatment, comprising:
a) providing the kit of claim 24;
b) combining the contents of the first, second, and third containers;
c) rectally administering the resulting combination of step b); and
d) orally administering the lipoic acid of the fourth container.

* * * * *